United States Patent [19]

Ellis, Jr. et al.

[11] Patent Number: 4,895,682
[45] Date of Patent: Jan. 23, 1990

[54] HYDROCARBON OXIDATIONS CATALYZED BY AZIDE-ACTIVATED METAL COORDINATION COMPLEXES

[75] Inventors: Paul E. Ellis, Jr., Downingtown; James E. Lyons, Wallingford; Harry K. Myers, Jr., Cochranville, all of Pa.

[73] Assignee: Sun Refining and Marketing Copany, Philadelphia, Pa.

[21] Appl. No.: 246

[22] Filed: Jan. 2, 1987

[51] Int. Cl.$^4$ ............... C07C 67/00; C07C 27/12; C07C 45/32

[52] U.S. Cl. ............... 260/410.9 R; 260/413; 560/241; 560/241.1; 562/512.2; 562/549; 568/398.8; 568/399; 568/910; 568/910.5

[58] Field of Search ............... 562/549, 512.2; 568/399, 398.8, 910, 910.5; 560/241, 241.1; 260/413, 410.9 R

[56] References Cited

U.S. PATENT DOCUMENTS 3,816,548  6/1974  Williams et al. ............... 568/399 X
3,873,625  3/1975  Barone ............... 568/399 X
4,028,423  6/1977  Brownstein et al. ............... 568/399 X
4,459,427  7/1984  Middleton et al. ............... 568/910 X

OTHER PUBLICATIONS

J. E. Lyons, Hydrocarbon Processing, Nov. 1980, p. 107, Table I.

Taylor et al., J. Chem. Soc. Chem. Comm., 279 (1984).
Mansuy et al., ibid., 253 (1983).
Groves et al., J. Am. Chem. Soc., 102, 6377 (1980).
Hill et al., ibid., 102, 6374 (1980).
Smegal et al., ibid., 105, 5515 (1983).
Tabushi et al., ibid., 103, 7371 (1981).

*Primary Examiner*—Werren B. Lone
*Attorney, Agent, or Firm*—J. Edward Hess; Donald R. Johnson

[57] ABSTRACT

Hydrocarbons, and particularly lower molecular weight alkanes and cycloalkanes, may readily be oxidixed with air or $O_2$ to form such products as alcohols, ketones, and the like selectively in high yields when there is employed as the catalyst a highly active azide-activated metal coordination complex having the structure

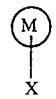

where M is a transition metal; "◯" is a ligand; and X is azide.

The invention is also directed to certain novel azide-activated metal coordination complex catalysts per se.

9 Claims, No Drawings

HYDROCARBON OXIDATIONS CATALYZED BY AZIDE-ACTIVATED METAL COORDINATION COMPLEXES

BACKGROUND OF THE INVENTION

1. Field of the Invention

This invention relates to a novel process for the oxidation of hydrocarbons. More particularly, this invention relates to the catalytic oxidation of a wide range of oxidizable hydrocarbons, particularly alkanes, with air or oxygen. The catalyst is a ligand complex of transition metals activated by an azide group bonded to the metal. Novel classes of these catalysts are also claimed herein.

2. Background of the Invention

The oxidation of alkanes and other aliphatic hydrocarbons catalyzed by transition metal complexes in the liquid phase is well known in the art, and commercial applications of this technology are extensive. See, for example, J. E. Lyons, Hydrocarbon Processing, Nov., 1980, page 107, Table I.

However, the oxidation of unactivated hydrocarbons such as methane, ethane, propane, butanes and the like by air or $0_2$ as the oxidant is extremely difficult to achieve. The use of macrocyclic metal complexes such as metalloporphyrins as catalysts in the liquid phase has not been successful in giving rapid rates and high selectivities under mild conditions using air or $0_2$ as the oxidant. Some success has been achieved using two less economically desirable approaches:

(1) The use of metalloporphyrin catalysts such as Fe(TPP)Cl and Mn(TPP)Cl (where TPP=the dianion of 5, 10, 15, 20-tetraphenylporphine) with iodosylbenzene, sodium hypochlorite, alkylhydroperoxides or other expensive, non-regenerable oxidants. [P. Traylor, D. Dolphin, and T. Traylor, *J. Chem. Soc. Chem. Comm.*, 279 (1984); J. Groves, W. Kruper, Jr., R. Haushalter, *J. Am. Chem. Soc.*, 102, 6377 (1980) C. Hill, B. Schardt, *J. Am. Chem. Soc.*, 102, 6374 (1980); J. Smegal and C. Hill, *J. Am. Chem. Soc.*, 105, 3515 (1983); A. Middleton and D. Smith, U.S. Pat. No. 4,459,427, (Jul. 10, 1984)]; or (2) The use of metalloporphyrin catalysts with molecular oxygen as oxidant and simultaneous addition of a reductant such as $NaBH_4$, ascorbic acid or colloidal platinum with $H_2$. Again, the added reagents are expensive and non-regenerable. Examples of this approach can be found in D. Mansuy, M. Fontecave and J. Bartoli, *J. Chem. Soc. Chem., Comm.* 253 (1983); I. Tabushi and A. Yazaki, *J. Am. Chem. Soc.*, 103, 7371 (1981).

It is, therefore, an object of this invention to provide an azide-activated metal coordination complex-catalyzed process for the oxidation of hydrocarbons, and particularly alkanes, using air or oxygen, but without the need for added expensive, non-regenerable oxidants, reductants, or other co-catalysts.

A further object of this invention is to provide certain novel azideactivated metal coordination complex catalysts per se for use in said process.

SUMMARY OF THE INVENTION

In accordance with the present invention, it has now been found that hydrocarbons generally, and alkanes in particular, desirably those hydrocarbons having from about 1 to 20 carbon atoms, and preferably those having from 1 to 10 carbon atoms, may readily be oxidized with air or oxygen to selectively form the corresponding hydrocarbon oxidation products such as acids, alcohols, ketones, esters, and the like, or mixtures thereof, when the catalyst is certain azide-activated metal coordination complexes, as defined below. More particularly, it has been found that coordinating an azide ion to certain metal coordination complexes can convert a complex which is otherwise catalytically inactive, or has low catalytic activity, into a highly active catalyst for the selective oxidation of difficult-to-oxidize alkanes to form alcohols, ketones, or mixtures thereof, in good yield with little burn to carbon oxides.

By virtue of the use of these catalysts in the oxidation of hydrocarbons, and especially alkanes, many surprising and unexpected advantages accrue. For example, the reaction can be carried out at lower temperatures than heretofore employed; there is often little or no cleavage of the starting material; there is little or no burn to form CO or $CO_2$; there is higher selectivity for alcohols, when alcohols are the desired product; the reaction rates are generally faster than those of comparable prior art processes; and the processes themselves are less expensive than those of the prior art which require strong oxidants. In some instances, such as the oxidation of ethane, propane, and the like, selective oxidations can be performed which have not been achieved to date, using the coordination complexes of this invention.

DESCRIPTION OF THE INVENTION

The process of this invention, which is applicable to hydrocarbons of virtually unlimited carbon atom content, is uniquely applicable to alkanes, which are known to be more difficult to oxidize than other types of hydrocarbons. However, it will be understood that the aforesaid catalysts are equally effective in the oxidation of other classes of hydrocarbons as well, especially those containing substituents which will enhance the reactivity of the carbon-hydrogen bond with oxygen, i.e. "activated hydrocarbons", as described below.

As aforestated, this process is particularly effective in the oxidation of alkanes, including cycloalkanes, substituted alkanes and the like. The alkane starting materials thus include straight and branch-chain compounds having from about 1 to 20 carbon atoms, preferably 1 to 10 carbon atoms such as methane, ethane, propane, n-butane, isobutane, n-pentane, n-hexane, 3-methylpentane, 2-methylpentane, heptane, 2-methylheptane, 3-methylheptane and the like, as well as cycloalkanes having from about 5 to 20 carbon atoms, preferably 5 to 10 carbon atoms, such as cyclohexane, cyclopentane, cycloheptane, cyclooctane, and the like. These compounds, if desired, may be substituted with various moieties, although care should be taken to exclude substituents which will adversely affect the activity of the catalyst.

When the foregoing alkanes are oxidized in accordance with the process of this invention, the corresponding alcohols, ketones, and the like are obtained. Thus, this process is generally applicable to the preparation of a broad class of known materials which may be used, for example, as solvents, chemical intermediates, commodity chemcials, polymer intermediates, gasoline additives, and the like.

Illustrations of activated hydrocarbons which may also be oxidized by the process of this invention include such compounds as toluene, xylenes, cumene, ethylbenzene, diphenylmethane, fluorene, and like alkyl-substitued aromatics having from about 7 to 20 carbon atoms, preferably 7 to 12 carbon atoms. Also included are olefinic hydrocarbons, particularly those containing allylic bonds, as, for example, propylene, butenes, cyclohexene, and the like. In addition, it should be understood that the catalysts of this process are able to oxidize olefinic double bonds directly in many instances to give epoxides, ketones and alcohols, which are also useful as solvents, chemical intermediates, and the like. The olefins desirably have from about 2 to 20 carbon atoms, preferably 2 to 8 carbon atoms.

Finally, the process of this invention is also applicable to the further oxidation of partially oxidized hydrocarbons other than, of course, organic acids. Thus, for example, partially-oxidized hydrocarbons such as alcohols and aldehydes may be oxidized to a more highly oxidized state, using the catalysts of this invention. Generally these partially oxidized hydrocarbons have from about 1 to 20 carbon atoms, that is, they are the same hydrocarbons as described above except for being partially oxidized.

Thus, from the foregoing description of the starting materials, it will be seen that this process is widely applicable to a broad range of oxidizable hydrocarbons, of which the oxidation of alkanes represents a preferred embodiment of this invention. As stated above, these hydrocarbons may contain various substituents on them as long as they do not adversely affect the activity of the catalyst.

The oxidation, which may be carried out in a generally known manner, is desirably conducted in the liquid phase, using such organic solvents as benzene, acetic acid, acetonitrile, methyl acetate, or like solvents which are inert to the conditions of the reactions, or in a neat solution of the hydrocarbon if it is liquid, and pressures ranging from about 15 to 1500 psig, preferably 30 to 750 psig, at temperatures of from about 25° to 250° C., more preferably 70° to 180° C. Depending upon whether the hydrocarbon to be oxidized is a solid, liquid, or gas, it is dissolved in or bubbled through the solvent, together with air or oxygen, in the presence of the aforementioned azide-activated metal coordination complex catalyst for periods of time sufficient to yield the desired oxidized product, generally from about 0.5 to 100 hours, and more preferably from 1 to 10 hours.

The nature of the solvent, while not critical, can have an effect on the rates and selectivities obtained and should be selected carefully in order to optimize the desired results. For example, it has been found that solvents such as acetonitrile and acetic acid are often very effective for the oxidation of alkanes to form oxygen-containing compounds, whereas reactions carried out in such solvents as methyl acetate or benzene may occur more slowly. Thus, by routine experimentation the optimum solvent for the particular process can readily be determined.

The ratios of the various reactants may vary widely, and are not critical. For example, the amount of catalyst employed can range from about $10^{-6}$ to $10^{-3}$ moles per mole of hydrocarbon such as alkane, and more preferably from about $10^{-5}$ to $10^{-4}$ moles of catalyst per mole of hydrocarbon, although other amounts are not precluded; while the amount of oxygen relative to the hydrocarbon starting material may vary widely, generally $10^{-2}$ to $10^2$ moles of oxygen per mole of hydrocarbon. Care should be taken since some of the ratios fall within explosive limits. As a group, the catalysts are almost always soluble unless used in large excess. Thus, as a rule the reactions are generally carried out as solution phase reactions.

Many of the catalysts employed in this process are generally known compounds, or else may readily be prepared in accordance with established methods. These catalysts, as mentioned above, may best be defined as azide-activated metal coordination complexes having the following general structure:

wherein M is a metal in the transition series from Groups IV(a) to VIII, such as Ti, V, Cr, Mn, Fe, Co, Nb, Mo, Ru, Rh, W, Os, Ir, or the like; X is azide ($N_3^-$); the component depicted as " ○ " comprises a ligand such as tetraphenylporphyrin, related porphyrinate ligands, porphycenes, porphenes, phthalocyanines, 1,3-bis (2-pyridylimino) isoindoline ("BPI"), and other 1,3-bis (arylimino) isoindolines, acetylacetonates, acetates, hydroxides, or a Schiff base such as salen, saleph, or the like. Thus, by the term "ligand", as used herein, is meant any group or system of atoms coordinated to a transition metal center which forms one or more bonds to the metal, as defined above, i.e. forms a coordination complex, and stabilizes this transition metal coordination complex in desirable oxidation states. Preferred among these ligands are such macrocyclic groups as porphyrins, phthalocyanines, BPI, 1,3-bis (arylimino) isoindolines, Schiff bases, and the like. Examples of other ligands which may be employed in the catalysts of this invention are such mono-, bi-, tri-, and tetradentate ligand systems as: hydroxides, acetates, propanates, butyrates, benzoates, naphthenates, stearates, acetylacetonates, and other $\beta$-diketones, 1,3-bis (arylimino) isoindolinates, salen, saleph, porphyrinates, porphycenates, porphenates, phthalocyanates, and like systems.

It is known in the art to halogenate ligands such as those described above in order to increase the oxidation resistance thereof, which thereby improves catalyst life. Usually, the halogen is chlorine or fluorine as in tetrachlorotetraphenylporphorinato. As used herein, the term ligand includes the halogenated type also.

In addition to the foregoing ligands there may also be employed in the catalyst of this invention such other ligands as bipyridines, terpyridines, phenanthrolines, dithiocarbamates, xanthates, salicylaldimines, cyclam, dioxocyclams, pyrazoylborates, and tetraazamacrocycles such as tetramethyltetraazadibenzocycloheptadecane.

The catalysts described and employed herein are either known or can readily be prepared by procedures described in the art, starting with known metal coordination complexes and/or literature preparations for making such complexes. In most cases the preparation of the catalysts of this invention involves reactions between known complexes having a metal halide, acetate, hydroxide or similar groups with either hydrazoic acid or sodium azide.

For example, Mn(TPP)Cl, Fe(TPP)Cl, and Cr(TPP)Cl metal complexes may be prepared by a standard method in which $TPPH_2$ (in which "TPP" is tetraphenylporphyrinato) and $Mn^{2+}$, $Fe^{2+}$, or $Cr^{3+}$ salts are refluxed together in a dimethylformamide solution. Purification is achieved by chromatography.

(See, e.g., A. D. Adler et al, *J. Inorg. Nucl. Chem.*, 32, 2443 (1970).) From these metal salts the corresponding azides may be prepared by metathesis reactions with dissolved $NaN_3$ or hydrazoic acid.

Similarly, $Mn(TPP)N_3$, $Cr(TPP)N_3$, $Mn(Por)N_3$, and $Cr(Por)N_3$ (where "Por" is porphyrinato) can be synthesized by the reaction of hydrazoic acid with the corresponding hydroxide of the metal coordination complex. (See, e.g., J. W. Buchler et al, *Z. Naturforsch,* 39*b*, 222–230 (1984) for preparation of these metal complexes.)

In a like manner, $Fe(TPP)N_3$ may be synthesized by reacting Fe(TPP)-0-(TPP)Fe with hydrazoic acid. (See D. A. Summerville et al, *JACS,* 98, 1747–1752 (1976).)

Also, Co(BPI)OAc (where "BPI" is 1,3-bis (2-pyridylimino) isoindoline) may be synthesized by the condensation of 1,2-dicyanobenzene with 2-aminopyridine in the presence of cobaltous acetate. Other 1,3-bis (arylimino) isoindolines are prepared similarly. (See W. O. Siegl, *J. Org. Chem.*, 42, 1872–78 (1977).) Co(BPI)N_3 may then be formed by reacting Co(BPI)OAc with $NaN_3$ in solution.

It is also possible to prepare azide transition metal coordination complexes by direct addition of azide ions. For example, novel metal phthalocyanine ("Pc") azide complexes such as $Cr(Pc)N_3$ and $Mn(Pc)N_3$ may be prepared by the following technique: In a Soxhlet extractor 400 ml of $NaN_3$ saturated anhydrous ethanol solution is refluxed under $N_2$. In the thimble is placed 2.0 g of Cr(Pc) or Mn(Pc). Reflux is continued until all of the solid Cr(Pc) or Mn(Pc) is extracted into the alcohol. The solution is filtered, evaporated to dryness and the solid $Cr(Pc)N_3$ or $Mn(Pc)N_3$ is washed thoroughly with distilled water to remove any residual $NaN_3$. Structures are confirmed by visible and infrared spectra:

| Complex | N—N Stretch in IR |
| --- | --- |
| $Cr(Pc)N_3$ | $2052\ cm^{-1}$ |
| $Mn(Pc)N_3$ | $2047\ cm^{-1}$ |

In a like manner those skilled in the art can readily prepare other azide catalysts by the general procedures and literature teachings described above.

From the foregoing it will be seen that these catalysts are comprised of three component parts: the ligand moiety, the transition metal which is bound to (i.e., complexed with) the ligand, and the azide group, which is bound to the transition metal. In some cases the dimers of the catalysts described above are suitable and should be regarded as the equivalent thereof, for example, the dimer of the azide of cobalt acetonylacetate. In these dimers, each of the two transitions metal moieties (M) is bound to each of the two azide moieties (X).

The nature of the X group, namely azide, which comprises the third component of the catalysts of this invention significantly affects the activity of the final catalyst. Surprisingly, other known groups such as chloride, acetate, benzoate and the like provide very poor if any results and should be avoided in the oxidation of most alkanes. While applicants do not wish to be bound by any particular theories, it is believed that the reason that the azide group is effective for purposes of activating the metal complexes of this invention is due to its electron-donating properties with respect to the transition metal component.

While the effectiveness of a particular catalyst may depend in part on the nature of the hydrocarbon starting material, selection of the catalyst for oxidizing any particular hydrocarbon can be readily determined by those skilled in the art. Examples of those catalysts which are most preferred, particularly for oxidation of lower alkanes, include such compounds as tetraphenylporphyrinato manganese (III) azide, tetraphenylporphyrinato chromium (III) azide, phthalocyaninato manganese (III) azide, phthalocyaninato chromium (III) azide, and the like.

The process of this invention will now be illustrated by, but is not intended to be limited to, the following examples.

EXAMPLES

A series of runs were carried out employing a variety of catalysts, alkanes, solvents, and operating conditions, as shown in Tables I to V below, together with the resulting products.

Except where shown otherwise in the tables, these runs were carried out as follows: the alkane was dissolved in an appropriate solvent containing the catalyst, and oxygen was added to the desired pressure. Oxidation was carried out at the designated temperature for the time listed in the tables. Gases and liquid products were analyzed by GC and MS.

In the following examples, activity is measured in terms of "turn over number" (T.O.N.), i.e., in terms of moles of $O_2$ consumed/mole of catalyst unless otherwise indicated in the tables, TBA and IPA are t-butyl and isopropyl alcohol respectively, (acac) is acetylacetonate, TPP is tetraphenylporphorinato, Pc is phthalocyaninato, selectivity is moles TBA product X 100/moles of isobutane reacted.

TABLE I

EFFECTS OF AZIDE ON COBALT - CATALYZED OXIDATION OF ISOBUTANE[a]

| EXAMPLE | CATALYST | mmoles | $O_2$ UPTAKE (mmoles) | T.O.N. | PRODUCTS (mmoles) ACETONE | TBA | $O_2$ COVERTED TO ACETONE + TBA (mmoles) | ISOBUTANE REACTED - (MOL %) | SELECTIVITY |
| --- | --- | --- | --- | --- | --- | --- | --- | --- | --- |
| 1 | None | — | 0 | — | 0 | 0 | 0 | 0 | — |
| 2 | AIBN[b] | 1.0 | 4.9 | 5 | 1.2 | 4.2 | 5.1 | 3.5 | 78 |
| 3 | AIBN | 0.10 | 1.7 | 17 | 0.3 | 0.7 | 1.1 | 1.0 | 70 |
| 4 | $Co(acac)_3$ | 0.10 | 1.5 | 15 | 0.3 | 2.1 | 1.8 | 2.2 | 88 |
| 5 | $Co(acac)_3$ | 0.025 | 0.9 | 36 | 0.2 | 0.8 | 0.9 | 0.9 | 80 |
| 6 | $Co(acac)_3$ + $NaN_3$ | 0.05 0.05 | 3.7 | 74 | 0.3 | 2.2 | 1.9 | 2.2 | 88 |
| 7 | $Co(acac)_2$ | 0.10 | 5.2 | 52 | 0.54 | 4.5 | 3.1 | 4.0 | 89 |
| 8 | $Co(acac)_2$ + $NaN_3$ | 0.05 0.05 | 4.6 | 93 | 0.24 | 1.9 | 1.3 | 1.9 | 89 |
| 9 | Co(BPI)OAc | 0.025 | 0.6 | 24 | Low | Low | Low | Low | NA |

TABLE I-continued
EFFECTS OF AZIDE ON COBALT - CATALYZED OXIDATION OF ISOBUTANE[a]

| EXAMPLE | CATALYST | mmoles | O₂ UPTAKE (mmoles) | T.O.N. | PRODUCTS (mmoles) ACETONE | TBA | O₂ COVERTED TO ACETONE + TBA (mmoles) | ISOBUTANE REACTED - (MOL %) | SELECTIVITY |
|---|---|---|---|---|---|---|---|---|---|
| 10 | Co(BPI)N₃ | 0.025 | 4.9 | 196 | 0.7 | 4.7 | 4.1 | 5.2 | 87 |

[a]Isobutane, 6–7 grams, in 25 ml benzene, oxidized at 80° C., O₂ partial pressure - about 75 psig, for 6 hours.
[b]AIBN = axobisiobutyronitrile

TABLE II
EFFECTS OF AZIDE ON MANGANESE-CATALYZED OXIDATION OF ISOBUTANE[a]

| EXAMPLE | CATALYST | mmoles | O₂ UPTAKE (mmoles) | T.O.N. | PRODUCTS (mmoles) ACETONE | TBA | O₂ COVERTED TO ACETONE + TBA (mmoles) | ISOBUTANE REACTED - (MOL %) | SELECTIVITY |
|---|---|---|---|---|---|---|---|---|---|
| 11 | Mn(acac)₃ | 0.025 | 0 | — | 0 | 0 | 0 | 0 | — |
| 12 | Mn(TPP)Cl | 0.05 | 0 | — | 0 | 0 | 0 | 0 | — |
| 13 | Mn(TPP)OAc | 0.05 | 0 | — | 0 | 0 | 0 | 0 | — |
| 14 | Mn(TPP)N₃ | 0.025 | 5.5 | 220 | 0.7 | 6.2 | 4.9 | 5.6 | 90 |
| 15 | Mn(TPP)N₃ | 0.013 | 2.3 | 177 | 0.4 | 3.0 | 2.5 | 2.7 | 88 |
| 16 | Mn(Pc)N₃ | 0.028 | 4.5 | 161 | 0.6 | 3.2 | 3.6 | 4.5 | 88 |
| 17 | Mn(Pc)N₃ | 0.013 | 3.7 | 285 | NA | NA | NA | NA | NA |
| 18 | Mn(Pc)N₃ | 0.007 | 2.3 | 330 | NA | NA | NA | NA | NA |

[a]Isobutane, 6–7 grams, in 25 ml benzene, oxidized at 80° C., O₂ partial pressure - about 75 psig, for 6 hours.

TABLE III
EFFECTS OF AZIDE ON CHROMIUM-CATALYZED OXIDATION OF ISOBUTANE[a]

| EXAMPLE | CATALYST | mmoles | O₂ UPTAKE (mmoles) | T.O.N. | PRODUCTS (mmoles) ACETONE | TBA | O₂ COVERTED TO ACETONE + TBA (mmoles) | ISOBUTANE REACTED - (MOL %) | SELECTIVITY |
|---|---|---|---|---|---|---|---|---|---|
| 19 | Cr(acac)₃ | 0.025 | 0 | — | 0 | 0 | 0 | 0 | — |
| 20 | Cr(TPP)Cl | 0.025 | 0 | — | 0 | 0 | 0 | 0 | |
| 21 | Cr(TPP)N₃ | 0.013 | 3.4 | 262 | 0.4 | 3.3 | 2.7 | 3.5 | 89 |
| 22 | Cr(TPP)N₃ | 0.025 | 6.6 | 264 | 0.8 | 6.3 | 5.2 | 6.7 | 88 |
| 23 | Cr(TPP)N₃ | 0.040 | 8.7 | 218 | 1.3 | 8.7 | 7.5 | 7.7 | 87 |
| 24 | Cr(acac)₃ | 0.05 | 2.6 | 52 | NA | NA | NA | NA | NA |

[a]Isobutane, 6–7 grams, in 25 ml benzene, oxidized at 80° C., O₂ partial pressure - about 75 psig, for 6 hours.

TABLE IV
OXIDATION OF ISOBUTANE AT 100° C. USING FIRST ROW METAL PORPHYRINATO AZIDES AS CATALYSTS[a]

| EXAMPLE | CATALYST | mmoles | SOLVENT | i-C₄H₁₀ (mmoles) | REACT. TIME (hrs.) | O₂ UPTAKE (mmoles) | T.O.N. | PRODUCTS (mmoles) ACETONE | TBA | ISOBUTANE CONVERTED ACETONE + TBA (Mol %) |
|---|---|---|---|---|---|---|---|---|---|---|
| 25 | None | — | Benzene | 117 | 6 | 0 | — | 0 | 0 | — |
| 26 | Cr(TPP)N₃ | 0.042 | Benzene | 105 | 2.5 | 7.2 | 172 | 1.3 | 3.7 | 4.8 |
| 27 | Mn(TPP)N₃ | 0.043 | Benzene | 103 | 6 | 11.9 | 282 | 1.9 | 7.9 | 9.5 |
| 28 | Fe(TPP)N₃ | 0.042 | Benzene | 116 | 6 | 3.8 | 90 | 1.5 | 3.1 | 4.0 |
| 29 | Cr(TPP)N₃ | 0.042 | 1/1 Benzene/CH₃CN | 81 | 5 | 5.2 | 124 | 1.6 | 2.8 | 5.4 |
| 30 | Mn(TPP)N₃ | 0.042 | 1/1 Benzene/CH₃CN | 66 | 7 | 10.1 | 241 | 2.6 | 5.5 | 12.3 |

[a]Isobutane was dissolved in 25 ml of solvent containing the catalyst. Oxygen was added and oxidations were run at 100° C. and 110–90 psig. Gas and liquid product analysis were done by GC.

TABLE V
EFFECTS OF AZIDE ON METAL CATALYZED OXIDATION OF PROPANE[a]

| EXAMPLE | CATALYST | moles/l | REACTION TIME (HRS) | PRODUCTS mmol/gram Reaction Mixture ACETONE | IPA | T.O.N. Mole Product/ Mole Catalyst |
|---|---|---|---|---|---|---|
| 31 | Co(acac)₃ | 0.032 | 5.0 | 0.14 | 0.19 | 57 |
| 32 | Co(acac)₃ | 0.032 | 12.8 | 0.26 | 0.15 | 89 |
| 33 | Co(acac)₃ | 0.032 | 60.5 | 0.23 | 0.17 | 87 |
| 34 | Co(BPI)N₃ | 0.02 | 13.1 | 0.24 | 0.13 | 132 |
| 35 | Co(BPI)N₃ | 0.02 | 61.5 | 0.24 | 0.13 | 131 |
| 36 | Mn(Pc)N₃ | 0.006 | 14.1 | 0.18 | 0.13 | 362 |
| 37 | Cr(TPP)N₃ | 0.006 | 13.4 | 0.20 | 0.12 | 377 |

[a]Catalyst dissolved in 7 ml benzene. Propane oxidized by air at 80 bars total pressure, i.e. about 1200 psig, at 150° C.

From the foregoing results in Tables I–V it will be seen that (1) reactions run with no catalyst give no products; (2) initiators and coordination complexes alone give, at best, modest activity as shown by the turn over number; (3) by adding an azide such as sodium azide separately improves activity (T.O.N.); while coordinating azide with the metal complex gives the best results, e.g. Examples 10 and 14–18.

were completely inactive (with the exception of Fe(TPP)OAc which has some activity), Cr(TPP)N$_3$, Fe(TPP)N$_3$ and Mn(TPP)N$_3$ were quite active catalysts.

TABLE VI

CYCLOHEXANE OXIDATION[a]
USING METALLOPORPHYRIN CATALYSTS

| EX-AMPLE | CATALYST | MMOLE CATALYST | SOL-VENT | PRESSURE (psig) | PRODUCT (MMOLE) CYCLOHEXANOL | PRODUCT (MMOLE) CYCLOHEXANONE | T.O.N.[b] | AVE. T.O.N./HR |
|---|---|---|---|---|---|---|---|---|
| 41 | Cr(TPP)Cl | 0.1750 | neat | 500 | 0.00 | 0.00 | 0 | 0 |
| 42 | CR(TPP)N$_3$ | 0.088 | neat | 500 | 5.90 | 5.32 | 128 | 28 |
| 43 | CR(TPP)N$_3$ | 0.088 | neat | 500 | 5.25 | 5.52 | 122 | 28 |
| 44 | CR(TPP)N$_3$ | 0.088 | neat | 125 | 6.82 | 9.22 | 182 | 36 |
| 45 | CR(TPP)N$_3$ | 0.088 | neat | 250 | 5.34 | 7.74 | 149 | 27 |
| 46 | CR(TPP)N$_3$ | 0.173 | neat | 500 | 6.95 | 8.67 | 106 | 12 |
| 47 | CR(TPP)N$_3$ | 0.044 | neat | 500 | 3.01 | 3.55 | 149 | 25 |
| 48 | CR(TPP)N$_3$ | 0.088 | neat | 500 | 5.34 | 5.78 | 126 | 27 |
| 49 | Fe(TPP)Cl | 0.1750 | neat | 500 | 0.00 | 0.00 | 0 | 0 |
| 50 | Fe(TPP)N$_3$ | 0.088 | neat | 500 | 3.01 | 3.97 | 79 | 18 |
| 51 | Fe(TPP)N$_3$ | 0.08 | neat | 500 | 8.19 | 11.00 | 218 | 18 |
| 52 | Fe(TPP)N$_3$ | 0.088 | neat | 500 | 7.30 | 9.62 | 192 | 48 |
| 53 | Fe(TPP)N$_3$ | 0.173 | neat | 500 | 7.95 | 10.15 | 105 | 16 |
| 54 | Fe(TPP)OAc | 0.173 | neat | 500 | 12.90 | 9.55 | 130 | 12 |
| 55 | Mn(TPP)OAc | 0.2500 | neat | 500 | 0.00 | 0.00 | 0 | 0 |
| 56 | Mn(Pc) | 0.2500 | neat | 500 | 0.00 | 0.00 | 0 | 0 |
| 57 | Mn(TPP)N$_3$ | 0.173 | neat | 500 | 2.79 | 2.85 | 32 | 6 |
| 58 | MN(TPP)N$_3$ | 0.175 | CH$_3$CN | 500 | 2.40 | 2.60 | 29 | 4 |
| 59 | Mn(TPP)N$_3$ | 0.088 | neat | 500 | 2.67 | 3.42 | 69 | 10 |
| 60 | Mn(TPP)N$_3$ | 0.173 | neat | 500 | 12.30 | 20.80 | 191 | 10 |
| 61 | Mn(acac)$_3$ | 0.175 | neat | 500 | 0.25 | 1.50 | 20 | 2 |

[a]CONDITIONS: 100 cc solvent; 10% oxygen in nitrogen at a flow rate of 5–10 cc/min. Temp. = 100° C. except Ex. 52, which is 125° C.
[b]T.O.N. = moles of product (cyclohexanol and cyclohexanone)/mole of catalyst.

These results are clearly demonstrated, for example, in Table II where a typical manganese complex, Mn(acac)$_2$, or Mn(TPP) halides, acetates and the like (e.g. Exs. 11–13), give no oxidation. However, by replacing the Cl or OAc with N$_3$ provides a startlingly active isobutane oxidation catalyst. This pattern is clearly repeated in the remaining three tables as well as in the examples that follow.

EXAMPLES 38–40

Hexane, 15 ml, was oxidized in acetic acid, 15 ml, using 42 mg. of cobalt catalyst (see Exs. 38–40). The oxygen pressure was 100 psig and the reaction temperature was 100° C. The major reaction products as determined by standardized glpc. were 2-and 3-hexanol, 2-and 3-hexanone together with some C$_2$–C$_4$ carboxylic acids produced by C-C bond cleavage reactions. The catalytic activity, as measured by the moles O$_2$ taken up per mole of catalyst over the 6 hour reaction time is given in the examples below. It can be seen that while Co(BPI)OAc was inactive, adding sodium azide produced an active catalyst, and replacing acetate by coordinated azide, i.e. Co(BPI)N$_3$, produced the highest activity.

| Example | Catalyst | (T.O.N.) Moles O$_2$ Uptake/ Mole Cat. |
|---|---|---|
| 38 | Co(BPI)(OAc) | 0.0 |
| 39 | Co(BPI)(OAc) + NaN$_3$ (13 mg) | 20.2 |
| 40 | Co(BPI)N$_3$ | 26.0 |

EXAMPLES 41–61

Under the conditions listed in Table VI below, cyclohexane was oxidized to a mixture of cyclohexanol and cyclohexanone. Although conventional metal TPP complexes such as the chlorides, acetates and the like

EXAMPLE 62

A 30 ml Fisher-Porter Aerosol tube equipped with thermocouple, magnetic stirrer and gas inlet and sampling ports was charged with 17 mg of chromiumtetraphenylporphyrinatoazide and 30 ml of 2,3-dimethylbutene-2. After thorough flushing with oxygen, 60 psig of oxygen pressure was admitted to the aerosol tube and the tube heated to 80° C. with stirring. Reaction was run at 80° C. with vigorous stirring for three hours during which time the pressure was kept at 100 psig by continous addition of 10 psi increments of oxygen as it was consumed. After 3 hours, 210 mmoles of oxygen was consumed. GLPC analysis of the reaction product showed that about 200 mmoles of 2,3-dimethylbutene-2 had been consumed to produce four major products: acetone, tetramethylethylene oxide (TMEO) 2,3-dimethyl-2-hydroxybutene-1 and 2,3-dimethyl-2-hydroperoxybutene-1 with tetramethylethylene oxide being the predominant product.

EXAMPLE 63

Under the conditions of Example 62, but substituting chromiumphthalocyaninatoazide as catalyst, there were obtained fair yields of acetone, TMEO, 2,3-dimethyl-2-hydroxybutene-1 and 2,3-dimethyl-2-hydroperoxybutene-1.

EXAMPLE 64

Under the conditions of Example 62, but substituting manganesephthalocyaninatoazide as catalyst, high yields of acetone, TMEO, 2,3-dimethyl-2-hydroxybutene-1 and 2,3-dimethyl-2-hydroperoxybutene-1 were obtained.

EXAMPLE 65

Under the conditions of Example 62 but substituting manganesetetraphenylporphyrinatoazide as catalyst, high yields of acetone, TMEO, 2,3-dimethyl-2-hydroxybutene-1 and 2,3-dimethyl-2-hydroperoxybutene-1 were obtained.

EXAMPLE 66

Under the conditions of Example 65 except that reaction temperature was 22° C., 11% conversion of 2,3-dimethylbutene-2 was obtained and the major reaction products were acetone, TMEO, 2,3-dimethyl-2-hydroxybutene-1 and 2,3-dimethyl-2-hydroperoxybutene-1.

EXAMPLE 67

Under the conditions of Example 64 except that reaction temperature was 22° C., 2,3-dimethylbutene-2 was converted to acetone, TMEO, 2,3-dimethyl-2-hydroxybutene-1 and 2,3-dimethyl-2-hydroperoxybutene-1.

EXAMPLE 68

Under the conditions of Example 62 except that reaction temperature was 22° C., 2,3-dimethylbutene-2 was converted to acetone, TMEO, 2,3-dimethyl-2-hydroxybutene-1 and 2,3-dimethyl-2-hydroperoxybutene-1.

EXAMPLE 69

Under the conditions of Example 35 using $Mn(Pc)N_3$ as catalyst, ethane was oxidized to a small extent.

What we claim is:

1. In a process in which an alkane is selectively oxidized by contact with air or oxygen in the presence of a catalyst comprising a Group IV(a) to VIII transition metal coordination complex, the improvement which comprises activating said catalyst with an azide ion bonded to the transition metal.

2. The process according to claim 1 wherein the alkane has from 1 to about 20 carbon atoms.

3. The process according to claim 1 wherein said alkane has from 1 to about 10 carbon atoms.

4. The process according to any of claims 1, 2 or 3 wherein the products of the oxidation are alcohols, ketones, or mixtures thereof.

5. The process according to any of claim 1, 2 or 3 wherein the products of said oxidation are alcohols, ketones, acids, esters, or mixtures thereof.

6. The process according to any of claims 1, 2 or 3 wherein the oxidation is carried out in the presence of an organic solvent.

7. The process according to claim 1, 2 or 3 wherein the transition metal is selected from the group consisting of Ti, V, Cr, Mn, Fe, Co, Nb, Mo, Ru, Rh, W, Os and Ir.

8. The process according to any of claims 1, 2, or 3 wherein the transition metal coordination complex contains a member selected from the group consisting of porphycenes, porphyrins, phthalocyanines, acetylacetonates, acetates, hydroxides, Schiff bases, propanoates, butyrates, benzoates, naphthenates, stearates, bipyridines, terpyridines, phenanthrolines, dithiocarbamates, xanthates, cyclam, dioxocyclams, and pyrazoylborates.

9. The process according to claim 4 wherein the oxidation is carried out in the presence of an organic solvent.

* * * * *